(12) United States Patent
Troxler et al.

(10) Patent No.: US 8,973,426 B2
(45) Date of Patent: Mar. 10, 2015

(54) ALCOHOL DETECTOR AND METHOD

(75) Inventors: John E. Troxler, Logansport, IN (US); Jennifer A. Musall, Logansport, IN (US)

(73) Assignee: Carter Fuel Systems, LLC, Cleveland, OH (US)

( * ) Notice: Subject to any disclaimer, the term of this patent is extended or adjusted under 35 U.S.C. 154(b) by 224 days.

(21) Appl. No.: 13/332,959

(22) Filed: Dec. 21, 2011

(65) Prior Publication Data
US 2013/0160529 A1    Jun. 27, 2013

(51) Int. Cl.
*G01N 27/00* (2006.01)
(52) U.S. Cl.
USPC .......................................... 73/61.43; 73/61.61
(58) Field of Classification Search
CPC ...................................................... G01N 27/00
USPC .......... 73/61.41, 61.43, 61.62, 61.61; 436/60, 436/131, 132, 139–143, 164, 166; 252/408.1
See application file for complete search history.

(56) References Cited

U.S. PATENT DOCUMENTS

| 2,209,764 | A | | 7/1940 | Cassen et al. |
| 2,679,752 | A | | 6/1954 | Metler |
| 3,505,020 | A | | 4/1970 | Caldwell |
| 3,745,659 | A | | 7/1973 | Hsu |
| 4,070,154 | A | * | 1/1978 | Mascher et al. ............... 436/131 |
| 4,578,357 | A | | 3/1986 | Melpolder |
| 4,608,345 | A | * | 8/1986 | Feldman et al. ................ 436/60 |
| 4,717,671 | A | * | 1/1988 | Melpolder ....................... 436/39 |
| 5,095,844 | A | | 3/1992 | Alexander |
| 5,150,065 | A | | 9/1992 | Luna |
| 5,585,550 | A | * | 12/1996 | Frank ............................ 73/61.43 |
| 6,376,250 | B1 | * | 4/2002 | Mohtadi ........................ 436/40 |
| 6,536,264 | B1 | | 3/2003 | Flammersfeld et al. |
| 6,896,779 | B2 | | 5/2005 | Thomas, III et al. |
| 6,902,661 | B2 | | 6/2005 | Thomas, III et al. |
| 7,659,731 | B2 | * | 2/2010 | Lin et al. ....................... 324/693 |
| 2010/0211289 | A1 | * | 8/2010 | Yoshida et al. ................ 701/103 |
| 2010/0241362 | A1 | * | 9/2010 | Yoshikawa et al. ............. 702/24 |

* cited by examiner

*Primary Examiner* — Hezron E Williams
*Assistant Examiner* — Hoang Nguyen
(74) *Attorney, Agent, or Firm* — Jones Day

(57) ABSTRACT

An alcohol detector for detecting high concentrations of alcohol in a fuel tank and for providing evidence that the alcohol was present even after it has been removed. In one aspect, the alcohol detector includes a cathode and an anode of different materials and spaced from one another. The anode experiences galvanic corrosion at a faster rate when exposed to high concentrations of alcohol than it does when exposed to unleaded gasoline. Thus, the amount of corrosion present on the anode provides evidence of the past presence of an improper fuel in the fuel tank. In another aspect, the alcohol detector is a dye printed on a fuel pump. The dye visually changes color intensity in the presence of high concentrations of alcohol to provide evidence of the past presence of alcohol.

20 Claims, 4 Drawing Sheets

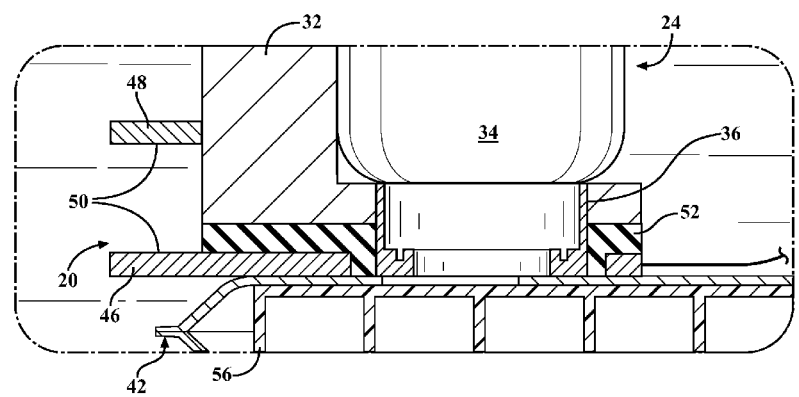
FIG. 3
FIG. 5
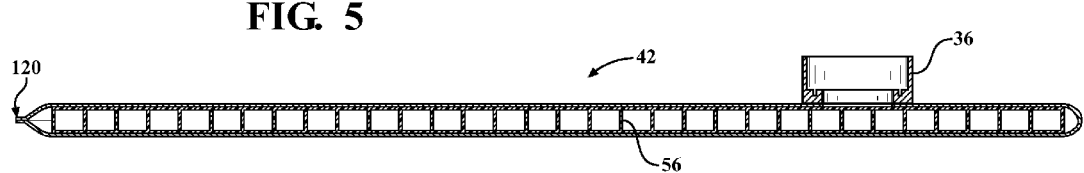

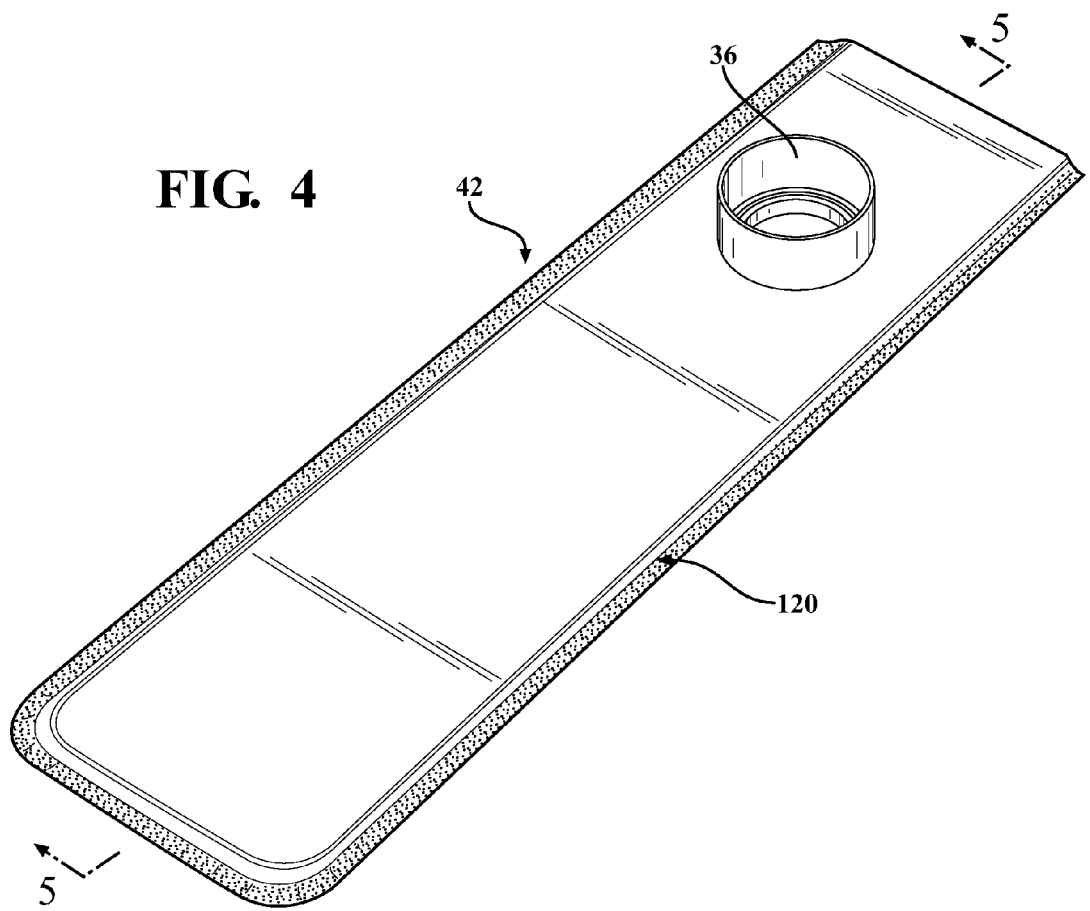

ALCOHOL DETECTOR AND METHOD

BACKGROUND OF THE INVENTION

1. Field of the Invention

The present invention is directed to an alcohol detection system, and more particularly to an alcohol detection system for detecting ethanol in a fuel pump.

2. Related Art

There is an increasing desire to power vehicles with ethanol, which is a product of renewable resources such as corn, soybeans or sugarcane, rather than gasoline, which is a byproduct of non-renewable crude oil. Unfortunately, high concentrations of ethanol may cause corrosion or other damage in the engine and fuel system components of many engines. Some components that are particularly vulnerable to damage from ethanol include fuel hoses and fuel pumps. Therefore, many automobile manufacturers have begun producing and selling "flex fuel vehicles" which are resistant to high concentrations of alcohol. Specifically, flex fuel vehicles are designed to operate on either unleaded gasoline or E-85, which is a blend of 85% ethanol and 15% unleaded gasoline. However, not all vehicles are flex fuel vehicles, and thus, many vehicles on the road today are susceptible to damage from E-85.

Gas stations typically sell E-85 in a separate pump from unleaded gasoline to reduce the likelihood of a customer accidentally filling his or her non-flex fuel vehicle with E-85. This separate pump also typically includes special warnings for informing drivers about the dangers of improperly using E-85 in a non-flex fuel vehicle. Regardless, many customers with non-flex fuel vehicles ignore the warnings or even disregard them because E-85 is often cheaper than unleaded gasoline. Thus, non-flex fuel vehicles are routinely damaged from the improper use of E-85.

If a vehicle is damaged from the use of E-85, the damage might not manifest itself until all of the E-85 has been consumed and the customer has refilled his or her fuel tank with unleaded gasoline. Thus, it is often difficult for a mechanic to determine whether damage on a vehicle was caused by a manufacturing defect, the repair of which is often covered by a manufacturer's warranty, or by the improper use of E-85, the repair of which is usually not covered by the manufacturer's warranty. In the absence of evidence that the customer is at fault for the damage to his or her vehicle, many mechanics simply repair the damaged vehicle under warranty at the manufacturer's expense. There remains a need for an improved system for detecting the presence of high concentrations of ethanol in a fuel tank and for providing evidence of ethanol even after it is no longer present in the fuel tank of the vehicle.

SUMMARY OF THE INVENTION

According to one aspect of the invention, a cathode and an anode are disposed in a fuel tank and spaced from one another by a predetermined distance. The anode is electrically grounded, and the cathode is in electrical communication with a power supply. The first and second metals have different nobilities, such either the anode or the cathode experiences galvanic corrosion in response to a voltage being applied across said anode and cathode. The rate of the galvanic corrosion depends, at least partially, on the electrical conductivity of the liquid in the fuel tank. Therefore, the amount of corrosion present on either the anode or cathode can be compared to a baseline amount of corrosion to determine whether an improper fuel, such as E-85, was present in the fuel tank. This evidence is beneficial because it allows vehicle manufacturers to avoid covering the cost of repairing vehicles damaged by customers using improper fuels in their vehicles.

According to another aspect of the invention, the anode and cathode are disposed on a fuel pump assembly, which is positioned adjacent the bottom of the fuel tank. This location is advantageous because the anode and cathode are submerged in the liquid in the fuel tank unless the fuel tank is empty or nearly empty. This location is also beneficial because the fuel pump can be easily removed from the fuel tank and inspected.

According to yet another aspect of the invention, a dye which is soluble in alcohol and insoluble in hydrocarbons is disposed on a fuel pump. The dye experiences a visually identifiable color change when exposed to alcohol, thus indicating that the fuel pump was exposed to an improper liquid. The intensity of the color change is determined at least partially on the concentration of the alcohol.

According to a further aspect of the invention, the dye is disposed along a seam on a strainer for the fuel pump. This location is advantageous because the dye is exposed to the liquid in the fuel tank without impeding the flow of fuel through the porous mesh of the strainer.

BRIEF DESCRIPTION OF THE DRAWINGS

These and other advantages and features of the present invention will be readily appreciated, as the same becomes better understood by reference to the following detailed description when considered in connection with the accompanying drawings wherein:

FIG. 3 is a cross-sectional and enlarged view of the inlet of the fuel pump of FIGS. 1 and 2;

FIG. 4 is a perspective and elevation view of a strainer including the second exemplary alcohol detector;

FIG. 5 is a cross-sectional view of the strainer of FIG. 4 taken along line 5-5 of FIG. 4.

DETAILED DESCRIPTION OF THE ENABLING EMBODIMENTS

Figure 1:
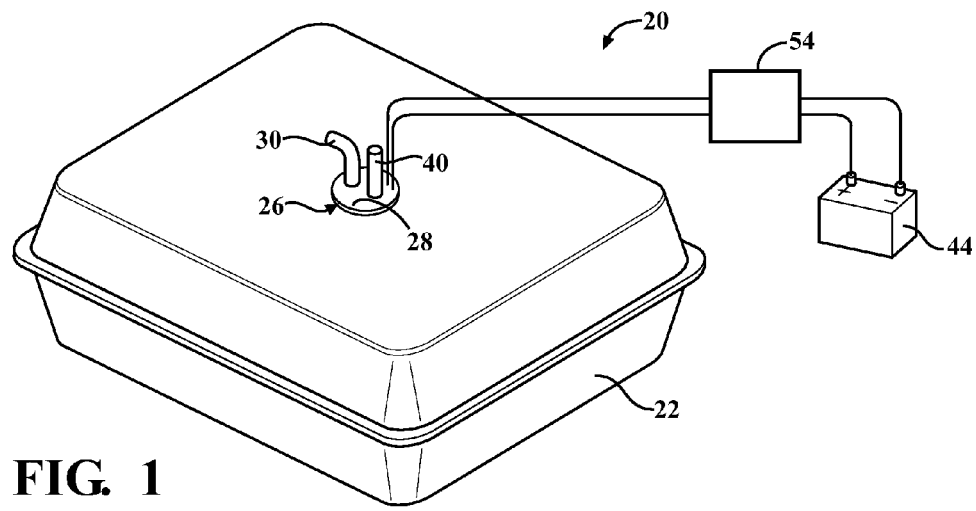
FIG. 1 is a perspective and elevation view of a fuel pump including the first exemplary alcohol detector.
Figure 2:
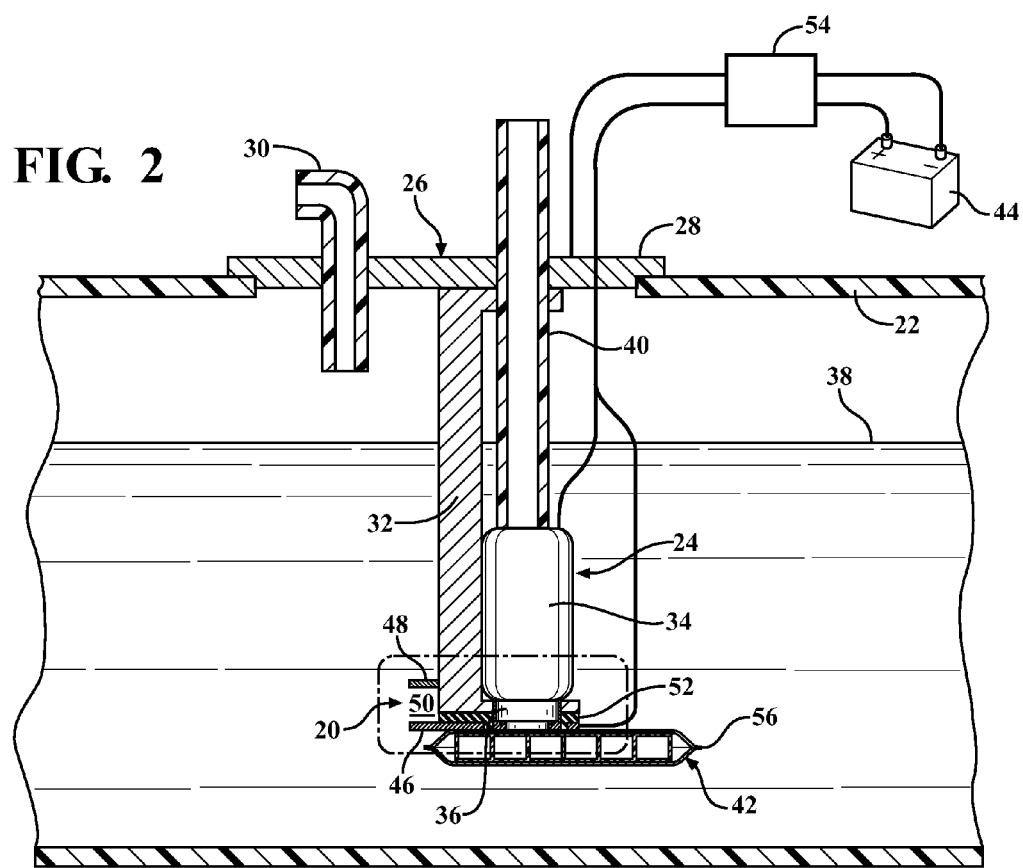
FIG. 2 is a cross-sectional view of the fuel pump of FIG. 1 and installed in a fuel tank.

Referring to the Figures, wherein like numerals indicate corresponding parts throughout the several views, a first exemplary alcohol detector 20 is generally indicated in FIGS. 1-3, and a second exemplary alcohol detector 120 is generally indicated in FIGS. 4 and 5. Both of the alcohol detectors 20, 120 are preferably for detecting the presence of a high concentrations of alcohol, such as ethanol, in fuel tanks 22 of automobiles and to provide evidence of the alcohol even after the alcohol is no longer in the fuel tank 22. However, the alcohol detectors 20, 120 could also find uses in a range of other non-automotive applications, such as boats, airplanes, motorcycles, snowmobiles, lawn mowers, etc. In addition to ethanol, the alcohol detectors 20, 120 can also detect the presence of other undesirable alcohols, such as methanol or tertiary butanol.

Both of the alcohol detectors 20, 120 are preferably for use in conjunction with a conventional fuel pump assembly 24 in a fuel tank 22 of the vehicle. Referring to FIG. 1, such a fuel pump assembly 24 typically includes a hanger 26 comprising a top plate 28, a return fuel line 30, a U-shaped bracket 32 and a fuel pump 34. The fuel pump 34 has an inlet 36 on its bottom side for receiving fuel 38 and an outlet hose 40, which extends upwardly through the hanger 26 for conveying fuel 38 to the engine of the vehicle. A strainer 42 is attached to the inlet 36 of the fuel pump 34 for filtering the fuel 38 before it leaves the fuel tank 22. As shown in FIG. 2, when the fuel pump assembly 24 is installed in the fuel tank 22 of a vehicle, the U-shaped bracket 32 supports the fuel pump 34 adjacent the bottom of the interior of the fuel tank 22. For reasons to be explained in further detail below, the top plate 28 and the U-shaped bracket 32 of the hanger 26 are preferably formed of an electrically conductive material, such as stainless steel.

The fuel pump 34 is preferably electrically powered and in electrical communication with a power supply 44. The electrically conductive hanger 26 can serve as the ground for the electric fuel pump 34. In operation, the fuel pump 34 propels fuel 38, such as unleaded gasoline, from the bottom of the fuel tank 22, through the outlet hose 40, and to the engine of the vehicle, as will be understood by those of skill in the art.

Referring now to FIG. 2, the first exemplary alcohol detector 20 includes a cathode plate 46 of a first electrically conductive metal and an anode plate 48 of a second electrically conductive metal different than the cathode plate 46. The cathode and anode plates 46, 48 are spaced from one another by a gap 50 of a predetermined length such that electricity can be conveyed between them when an electrolyte is disposed therebetween. In the exemplary embodiment, the cathode and anode plates 46, 48 are coupled to the U-shaped bracket 32 adjacent of the fuel pump 34 so that they are submerged in fuel 38, even when the fuel tank 22 is nearly empty. However, it should be appreciated that the cathode and anode plates 46, 48 could be disposed in any desirable location in the fuel tank 22 and do not have to be coupled to the fuel pump assembly 24.

An insulating layer 52 is disposed between the cathode plate 46 and the U-shaped bracket 32 to insulate the cathode plate 46 from the U-shaped bracket 32. The cathode plate 46 is also in electrical communication with the power supply 44 through the fuel pump 34 such that it is positively charged whenever the fuel pump 34 is operated. The cathode plate 46 could alternately be connected to the power supply 44 independently of the fuel pump 34, and the voltage could be applied to the cathode plate 46 continuously, or at predetermined intervals. Even further, the cathode plate 46 and power supply 44 could be electrically coupled to a controller 54 for controlling the magnitude of the voltage applied to the cathode plate 46 and for monitoring the duration that the voltage is applied.

In contrast to the cathode plate 46, the anode plate 48 is grounded by the U-shaped bracket 32 and remains neutrally charged. When the fuel pump 34 is in operation, the fuel 38 disposed in the gap 50 functions as an electrolyte to convey electricity from the cathode plate 46 to the anode plate 48. The amount of electricity conveyed depends at least partially on the electrical conductivity of the electrolyte. As will be discussed in further detail below, this conveyance of electricity through the electrolyte will cause corrosion in one of the cathode and anode plates 46, 48.

It is well known that when two metals are submerged in an electrolyte and electricity is conveyed therebetween, the less noble of the metals will experience galvanic corrosion. In the first exemplary fuel 38 detector, the first metal of the anode plate 48 is less noble than the second metal of the cathode plate 46. Therefore, in the first exemplary fuel 38 detector, the anode plate 48 experiences galvanic corrosion whenever the fuel pump 34 is operated. In at least one embodiment, the cathode plate 46 is of stainless steel, and the anode plate 48 is of aluminum, tin or zinc. However, it should be appreciated that both of these plates 46, 48 could be formed of a wide range of different materials. It should also be appreciated that the cathode plate 46 could be of the less noble metal, if desired, and thus, the cathode plate 46 could experience the galvanic corrosion rather than the anode plate 48.

The rate of corrosion in the anode plate 48 depends primarily on the following factors: (1) the magnitude of the voltage applied to the cathode plate 46; (2) the duration of the voltage; (3) the nobility of the first and second metals; (4) the gap 50 between the anode and cathode plates 48, 46; and (5) the electrical conductivity of the electrolyte. In the first exemplary alcohol detector 20, factors (1)-(4) are all known or can be measured, e.g. with the controller 54 or any other sensor. Therefore, the amount of corrosion on the anode plate 48 can be estimated if only the proper fuel 38 is used in the fuel tank 22. The amount of corrosion to be expected for a range of durations is stored in a database, preferably accessible through the internet. The database is made available to mechanics so that they can input the duration of the voltage applied to the cathode plate 46 and receive a baseline amount of corrosion to compare with the anode plate 48 of the vehicle.

Most alcohols, including ethanol, are more electrically conductive than unleaded gasoline. Therefore, the anode plate 48 will corrode at a faster rate when the first exemplary alcohol detector 20 is submerged in high concentrations of alcohol, such as E-85, as compared to unleaded gasoline. Therefore, if the corrosion on the anode plate 48 of a vehicle is greater than the baseline amount of corrosion shown in the database, then a mechanic has evidence that E-85, or some other improper liquid, was present in the fuel tank 22. If the mechanic determines that the improper fuel 38 was the cause of the vehicle's problems, then the vehicle manufacturer can choose not to pay for the repairs under the manufacturer's warranty.

The second exemplary alcohol detector 120 is a dye disposed on a strainer 42 (commonly known as a fuel sock) of a conventional fuel pump assembly 24, such as the fuel pump assembly 24 discussed above and shown in FIG. 1. An exemplary strainer 42 is generally shown in FIGS. 4 and 5. The strainer 42 includes a single sheet of a porous mesh material and an injection molded stuffer 56 of an injection molded plastic material or of an extruded tubular mesh construction. The exemplary strainer 42 is formed by cutting a hole the sheet of porous mesh material and attaching the inlet 36 of the fuel pump 34 to the hole. The sheet of mesh material is then folded in half with the stuffer 56 being positioned between the two halves. Three sides of the perimeter are then ultrasonically welded together to enclose the stuffer 56 in an interior of the strainer 42. In operation, when the fuel pump 34 is operated, fuel 38 is filtered from the pores of the mesh and into the interior of the strainer 42. The filtered fuel 38 is then delivered to the fuel 38 filter through the inlet 36. It should be appreciated that the strainer 42 could be constructed in many other ways and could take any desirable shape, as will be understood by those of skill in the art.

The dye disposed on the strainer 42 is soluble in alcohol and insoluble in hydrocarbons (unleaded gasoline). The dye is preferably of the type described in U.S. Pat. No. 4,608,345, issued to Feldman et al. on Aug. 26, 1986, which is hexamethyl p-rosaniline chloride, bromophenol blue or bromocresol green. The dye is also mixed with an alcohol insoluble, hydrocarbon insoluble solid, such as calcium, magnesium, barium or calcium carbonate. However, it should be appreciated that a variety of other dyes or solutions could alternately employed.

The dye changes color in the presence of alcohol and does not return to its original color after the alcohol is gone. In the exemplary embodiment, the dye is only disposed along the seam between the halves of the porous mesh. The seam is continuously exposed to the fluid in the fuel tank 22, but in this location, the dye thus does not compromise the flow of fuel 38 from the fuel tank 22 to the interior of the strainer 42. The strainer 42 is a particularly advantageous location for the dye because it is adjacent the bottom of the fuel tank 22, and thus, it is exposed to fluid even when the fuel tank 22 is mostly empty. However, it should be appreciated that the dye could alternately be disposed on any other location of the fuel pump assembly 24.

The color of the dye changes more rapidly in high concentrations of alcohol than in low concentrations of alcohol. Thus, the color that of the dye if it is only exposed to proper fuels, e.g. unleaded gasoline with a low concentration of ethanol, can be estimated as a function of the duration of time since the strainer 42 was first exposed to fuel 38 (assuming the fuel tank 22 is never entirely emptied). Unlike the first exemplary alcohol detector 20 described above, this dye does not rely on the passage of current. Therefore, if a vehicle owner brings his or her vehicle to a mechanic merely has to determine when the fuel tank 22 was first installed in the vehicle and filled with fuel 38. Typically, this can be done by cross-referencing the vehicle's vehicle identification number (YIN) with the vehicle manufacturer's database. The mechanic can then input this duration into another database to determine a baseline color of the dye if only exposed to proper fuels 38. If the dye has changed color at an increased rate, then the mechanic has evidence that E-85 or a high concentration of another improper alcohol, has been present in the fuel tank 22 of the vehicle and may have caused the damage. If the improper fuel 38 was the cause of the vehicle's problems, then the vehicle manufacturer can choose not to cover the repairs under the manufacturer's warranty.

Figure 6:
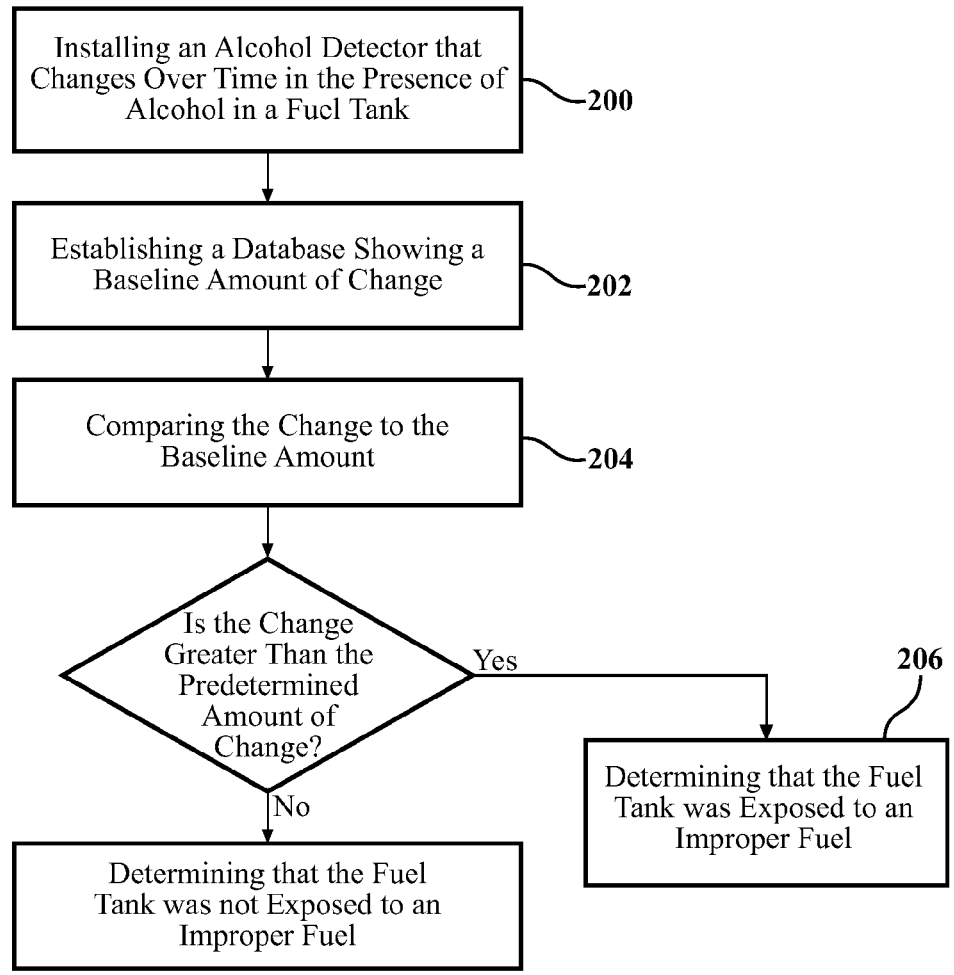
FIG. 6 is a flow chart of a method of detecting alcohol in a fuel tank.

FIG. 6 shows a flow chart of a method of detecting alcohol in a fuel tank 22 of a vehicle. The method starts with the step 200 of installing an alcohol detector that changes over time in the presence of alcohol in the fuel tank 22. The method continues with the step 202 of establishing a database showing a baseline amount of change in the alcohol detector after exposure for a range of durations solely to hydrocarbon fuels 38 with low concentrations of alcohol. After a known duration of exposure to fluid in the fuel tank 22, the method proceeds with the step 204 of comparing the change of the alcohol detector to the baseline amount of change shown in the database. Finally, the method includes the step 206 of determining that the fuel pump 34 was exposed to high concentrations of alcohol in response to the change in the alcohol detector being greater than the baseline amount of change.

Obviously, many modifications and variations of the present invention are possible in light of the above teachings and may be practiced otherwise than as specifically described while within the scope of the appended claims.

What is claimed is:

1. An alcohol detector for detecting alcohol in a fuel tank, the alcohol detector comprising:
   a dye disposed on a fuel pump assembly in the fuel tank, the dye being soluble in alcohol and insoluble in hydrocarbons for changing colors in the presence of alcohol; and
   a strainer for filtering fuel, wherein the strainer is of a one piece porous mesh material folded over a stuffer to present an interior of the strainer, wherein the porous mesh material is ultrasonically welded to itself along three edges to present a seam, and wherein the dye is disposed on the seam of the strainer.

2. The alcohol detector of claim 1 wherein said dye includes at least one of hexamethyl p-rosaniline chloride, bromophenol blue and bromocresol green.

3. The alcohol detector of claim 2 wherein the dye is mixed with a solid comprising at least one of calcium, magnesium, barium and calcium carbonate.

4. The alcohol detector of claim 1 wherein the seam is adjacent to a bottom of the fuel tank.

5. A method comprising:
   disposing a dye on a seam of a fuel pump assembly; and
   disposing the fuel pump assembly in a fuel tank of a vehicle;
   wherein the dye is soluble in alcohol and insoluble in hydrocarbons for changing colors in the presence of alcohol;
   wherein the fuel pump assembly includes, for filtering fuel, a strainer that is of a one piece porous mesh material folded over a stuffer to present an interior of the strainer; and
   wherein the porous mesh material is ultrasonically welded to itself along three edges to provide the seam.

6. The method of claim 5 further comprising, after the disposing step and after instances where the fuel tank was filled with fuel:
   determining a color of the dye on the seam.

7. The method of claim 6 further comprising:
   determining a duration of time that the dye has been exposed to fuel; and
   determining, based on the determined duration of time, a baseline color for the dye on the seam, the baseline color corresponding to a color the dye would have if the dye were not exposed to an excessive amount of alcohol.

8. The method of claim 7 further comprising:
   comparing the color of the dye on the seam to the baseline color to determine whether fuel that has been in the fuel tank contained an excessive amount of alcohol.

9. The method of claim 8 further comprising:
   determining, based on results of the comparing step, whether to cover a repair of the vehicle.

10. The method of claim 7 wherein the determining of the duration of time is based on a vehicle identification number (VIN) of the vehicle.

11. The method of claim 10 wherein the determining of the duration of time based on the VIN includes inputting the VIN into a database of a manufacturer of the vehicle to obtain the duration of time.

12. The method of claim 7 wherein the determining of the baseline color is based on inputting the determined duration of time into a data base that includes a correspondence between duration of time and baseline color.

13. A fuel pump assembly comprising:
   a pump that is configured to be contained in a fuel tank and configured to pump fuel that is contained in the fuel tank;
   a strainer attached to the pump, wherein the strainer is configured to be contained in the fuel tank and to be immersed in the fuel and to filter the fuel as the fuel enters the pump, wherein the strainer is of a one piece porous mesh material folded over a stuffer to present an interior of the strainer, and wherein the porous mesh material is ultrasonically welded to itself along three edges to form a seam; and
   a dye disposed on the seam, the dye being soluble in alcohol and insoluble in hydrocarbons for changing colors in the presence of alcohol.

14. The fuel pump assembly of claim 13 wherein the strainer is contained in the fuel tank.

15. The fuel pump assembly of claim 14 wherein the strainer is immersed in the fuel which is contained the fuel tank.

16. The fuel pump assembly of claim 14 wherein the seam is adjacent to a bottom of the fuel tank.

17. The fuel pump assembly of claim 13 wherein the dye includes at least of one of hexamethyl p-rosaniline chloride, bromophenol blue and bromocresol green.

18. The fuel pump assembly of claim 17 wherein the dye is mixed with a solid comprising at least one of calcium, magnesium, barium and calcium carbonate.

19. The fuel pump assembly of claim 13 wherein the dye is disposed only on the seam of the strainer and not elsewhere on the strainer.

20. The fuel pump assembly of claim 13 wherein the fuel tank is configured to contain gasoline.

* * * * *